United States Patent [19]

Larkin

[11] Patent Number: 4,985,582
[45] Date of Patent: Jan. 15, 1991

[54] PESTICIDAL COMPOUNDS

[75] Inventor: John P. Larkin, Leighton Buzzard, England

[73] Assignee: The Wellcome Foundation Ltd., London, England

[21] Appl. No.: 401,490

[22] Filed: Sep. 1, 1989

Related U.S. Application Data

[63] Continuation of Ser. No. 911,913, Sep. 22, 1986, abandoned.

[30] Foreign Application Priority Data

Sep. 24, 1985 [GB] United Kingdom ............... 8523582
Jan. 6, 1986 [GB] United Kingdom ............... 8600201

[51] Int. Cl.$^5$ .......................................... C07C 321/04
[52] U.S. Cl. .................................. 558/388; 558/430; 558/432; 558/433; 558/434; 558/436; 568/56; 568/57; 568/62; 568/65; 568/66
[58] Field of Search ....................... 568/62, 66, 65, 56, 568/57; 558/388, 430, 432, 433, 434, 436

[56] References Cited

U.S. PATENT DOCUMENTS 2,864,867  12/1958  Miller .................................. 568/56

FOREIGN PATENT DOCUMENTS 0152229  1/1985  European Pat. Off. .
1399167  6/1975  United Kingdom .

OTHER PUBLICATIONS

C. Kolomyjec et al., Chem. Abstracts, vol. 99, No. 63185d (1983).
C. Kolomyjec et al. Inorg. Chem. 22, 2343–2345 (1983).

Primary Examiner—Mary E. Ceperley
Attorney, Agent, or Firm—Nixon & Vanderhye

[57] ABSTRACT

Bicyclo-[2,2,1]-heptanes, bicyclo-[2,2,2]-octanes and bicyclo-[2,2,3]-nonanes, having 2 or 3 ring hetero atoms selected from O, S and N substituted at the 1-position by a carbocyclic group other than an alkynylphenyl group, and substituted at the 4-position and optionally substituted at the 3 and/or 5 position, are valuable pesticides, particularly insecticides and acaricides. Various cyclization processes are disclosed to form the various bicyclo ring systems.

1 Claim, No Drawings

PESTICIDAL COMPOUNDS

This is a continuation of application Ser. No. 06/911,913 filed Sept. 22, 1986, now abandoned.

The present invention relates to novel chemical compounds having pesticidal activity to methods for their preparation, to compositions containing them and to their use in the control of pests. More particularly the invention relates to a class of heterabicycloalkanes.

The use of certain 2,6,7-trioxabicyclo[2,2,2]octanes as pesticides is disclosed in European Patent Application No. 152229; it has now been discovered that derivatives of these compounds in which at least one of the ring oxygens has been substituted have interesting pesticidal activity.

Accordingly the present invention provides a compound of the formula (I):

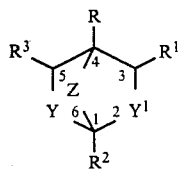
(I)

wherein R is $C_{2-10}$ alkyl, alkenyl or alkynyl, each optionally substituted by, or methyl substituted by, cyano, $C_{3-4}$ cycloalkyl, halo, $C_{1-4}$ alkoxy or a group $S(O)_mR^4$ where $R^4$ is $C_{1-4}$ alkyl and m is 0, 1 or 2; or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)_mR^4$ as defined hereinbefore;

$R^1$ is hydrogen, halo, a group $CO_2R^4$ wherein $R^4$ is $C_{1-4}$ alkyl, or $R^1$ is $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms or a group $S(O)_mR^4$ as defined hereinbefore or $R^1$ is cyano, gem dimethyl, spiro-cyclopropyl, gem dicyano, gem diethynyl, oxo or methylene optionally substituted by cyano, or trifluoromethyl, or $R^1$ is $C_{2-3}$ alkynyl substituted by tri $C_{1-4}$ alkylsilyl or $R^1$ and R and the carbon atoms to which they are attached form a $C_{5-7}$ carbocyclic ring optionally substituted by halo, $C_{1-3}$ alkyl or alkoxy, or $C_{2-3}$ alkenyl;

$R^2$ is phenyl, $C_{5-10}$ cycloalkyl or cycloalkenyl each optionally substituted;

$R^3$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo or $R^3$ is cyano or halo; and Y and $Y^1$ are the same or different and are each selected from oxygen or $S(O)_m$ where m is 0, 1 or 2 and Z is $CH_2CH_2$, $CH_2CH_2O$, sulphur, $CH_2O$, $CH_2S$, $CHR^{1x}NR^5$ wherein $R^{1x}$ is hydrogen, cyano, halo, a group $CO_2R^4$ or $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms or a group $S(O)_mR^4$ wherein m and $R^4$ are as hereinbefore defined and $R^5$ is hydrogen, benzyl, $C_{1-4}$ alkyl or $C(O)R^6$ wherein $R^6$ is $C_{1-4}$ alkyl, alkoxy or a group $NHR^7$ wherein $R^7$ is $C_{1-4}$ alkyl, $C_{7-8}$ aralkyl or phenyl optionally substituted by halo or Z is $-CH(OR^8)-CH_2$ wherein $R^8$ is hydrogen, $C_{1-4}$ alkyl, $C_{1-4}$ acyl, $C_{2-7}$ carbamoyl or a group $SO_2R^4$ wherein $R^4$ is $C_{1-4}$ alkyl or $-CH(OR^8)-CH_2-$ is $-CO.CH_2-$; provided: (i) that when Z is $CHR^{1x}NR^5$, $R^1$ and $R^3$ are hydrogen, (ii) that when Y and Y' are both oxygen, Z is not $CH_2O$, and (iii) that $R^2$ is not phenyl substituted by an optionally substituted $C_{2-3}$ alkynyl group.

In the definition of Z the first atom is adjacent to the 4-position of the bicyclic ring system.

Suitably R is propyl, butyl, pentyl, $C_{2-5}$ alkenyl or alkynyl, $C_{5-7}$ cycloalkyl or phenyl. Most suitably R is n-propyl, n-butyl, i-butyl, sec-butyl, t-butyl, cyclopentyl, cyclohexyl or phenyl and preferably R is n-propyl, n-butyl, i-butyl, t-butyl or cyclohexyl.

Suitably $R^1$ is hydrogen, cyano, ethynyl, methyl or ethyl optionally substituted by cyano, methoxy, methylthio or fluoro. Most suitably $R^1$ is hydrogen, methyl, cyano, trifluoromethyl or ethyl. Preferably $R^1$ is hydrogen, methyl or trifluoromethyl.

When $R^2$ is a substituted phenyl, $C_{5-10}$ cycloalkyl or cycloalkenyl group, suitable substituents include halo, cyano, azido, nitro, $C_{1-3}$ alkyl or alkoxy optionally substituted by halo or $C_{2-3}$ alkenyl optionally substituted by halo. Suitably when $R^2$ is phenyl it is substituted by up to three substituents which are preferably at the 3,4 and/or 5-positions.

Suitably $R^2$ is cyclohexyl, cycloheptyl or phenyl optionally substituted at the 3-,4- and/or 5 position by chloro, bromo, iodo, cyano, azido or nitro and/or phenyl optionally substituted at the 2- and/or 6-position by fluoro. Most suitably $R^2$ is cyclohexyl or phenyl optionally substituted at the 4-position by chloro, bromo iodo or cyano.

Suitably $R^3$ is hydrogen or $C_{1-3}$ alkyl, preferably $R^3$ is hydrogen.

Suitably Z is $-CH_2S-$, $-CH_2O-$ or $-CH_2CH_2-$. Preferably Z is $-CH_2S-$ or $-CH_2O-$.

Suitably Y and $Y^1$ are both oxygen or both sulphur.

One group of compounds of formula (I) is that of formula (IA):

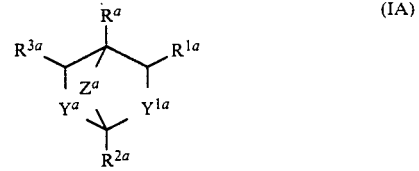
(IA)

wherein $R^a$ is $C_{2-7}$ alkyl, alkenyl or alkynyl, each optionally substituted by cyano halogen or $C_{1-4}$ alkoxy, or $R^a$ is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halogen or cyano; $R^{1a}$ is hydrogen, $C_{1-3}$ alkyl, $C_{2-3}$ alkenyl or alkynyl each optionally substituted by cyano, $C_{1-4}$ alkoxy, $C_{1-4}$ alkylthio, alkyl carbalkoxy containing up to 6 carbon atoms or halo, or $R^{1a}$ is cyano, gem dimethyl or $R^{1a}$ and $R^a$ and the carbon atoms to which they are attached form a $C_{5-7}$ carbocyclic ring optionally substituted by $C_{1-3}$ alkyl or alkoxy, $R^{2a}$ is phenyl, $C_{5-10}$ cycloalkyl or cycloalkenyl each optionally substituted and $R^{3a}$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo; $Y^a$ and $Y^{1a}$ are the same or different and are each selected from oxygen and $S(O)_{m^a}$ where $m^a$ is 0, 1 or 2; $Z^a$ is $CH_2CH_2$, $CH_2CH_2O$, sulphur, $CH_2O$, $CH_2S$, $CH_2NR^{4a}$ wherein $R^{4a}$ is hydrogen, $C_{1-4}$ alkyl, benzyl or $C(O)R^{5a}$ wherein $R^{5a}$ is $C_{1-4}$ alkyl or alkoxy, or $Z^a$ is $-CH(OR^{6a})CH_2-$ wherein $R^{6a}$ is hydrogen, $C_{1-4}$ alkyl or $C_{1-4}$ acyl or $-CH(OR^{6a})-CH_2-$ is $-CO.CH_2-$; except that when $Y^a$ and $Y^{1a}$ are both oxygen, then $Z^a$ is not $CH_2O$.

Suitably R$^a$ is propyl, butyl, C$_{5-7}$ cycloalkyl or phenyl. Most suitably R$^a$ is n-propyl, t-butyl, cyclopentyl or cyclohexyl and preferably R$^a$ is n-propyl, t-butyl or cyclohexyl.

Suitably R$^{1a}$ is hydrogen cyano, methyl or ethyl optionally substituted by cyano, methoxy, methylthio or fluoro. Most suitably R$^{1a}$ is hydrogen, methyl, trifluoromethyl or ethyl. Preferably R$^{1a}$ is hydrogen or methyl.

When R$^{2a}$ is a substituted phenyl, C$_{5-10}$ cycloalkyl or cycloalkenyl group, suitable substituents include halo, cyano, azido, nitro, C$_{1-3}$ alkyl optionally substituted by halo or C$_{2-3}$ alkenyl or alkynyl each optionally substituted by halo.

Suitably R$^{2a}$ is cyclohexyl, cycloheptyl or phenyl optionally substituted at the 3- or 4-position by halo, cyano, C$_{2-3}$ alkynyl, azido or nitro. Most suitably R$^{2a}$ is cyclohexyl or phenyl optionally substituted at the 4-position by chlorine, bromine, C$_{2-3}$ alkynyl or cyano.

When Z$^a$ contains a hetero atom this is adjacent to the carbon atom of the bicyclooctane ring having the substituent R$^{2a}$.

Suitably Z$^a$ is —CH$_2$S—, —CH$_2$CH$_2$O— or —CH$_2$CH$_2$—.

Suitably Y$^a$ and Y$^{1a}$ are both oxygen.

A further group of compounds of the formula (IA) is as defined above except that in addition to the values listed R$^{6a}$ can be C$_{3-7}$ carbamoyl.

Preferred compounds include
1-(4-bromophenyl)-4-i-butyl-2,6-dioxa-7-thiabicyclo[2,2,2]octane
1-(4-bromophenyl)-4-i-propyl-2,6-dioxa-7-thiabicyclo[2,2,2]octane
1-(4-bromophenyl)-4-s-butyl-2,6-dioxa-7-thiabicyclo[2,2,2]octane
1-(4-chlorophenyl)-4-s-butyl-2,6-dioxa-7-thiabicyclo[2,2,2]octane
4-s-butyl-1-cyclohexyl-2,6-dioxa-7-thiabicyclo[2,2,2]octane
1-(4-bromophenyl)-3-methyl-4-n-propyl-2,6-dioxa-7-thiabicyclo-[2,2,2]octane
1-cyclohexyl-5-n-propyl-2,7,8-trioxabicyclo[2,2,2]nonane
1-(4-chlorophenyl)-4-n-propyl-2,6-dioxabicyclo[2,2,2]octane
1-(4-bromophenyl)-4-n-propyl-2,6-dioxa-7-thiabicyclo[2,2,2]octane
4-t-butyl-1-(4-chlorophenyl)-2,6-dioxabicyclo[2,2,2]octane
1-(4-chlorophenyl)-8-hydroxy-4-n-propyl-2,6-dioxabicyclo[2,2,2]octane
1-(4-chlorophenyl)-8-methoxy-4-n-propyl-2,6-dioxabicyclo[2,2,2]octane
1-(4-chlorophenyl)-8-oxo-4-n-propyl-2,6-dioxabicyclo[2,2,2]octane
1-(4-bromophenyl)-4-t-butyl-2,6-dioxa-7-thiabicyclo[2,2,2]octane
4-t-butyl-1-(4-chlorophenyl)-2,6-dioxa-7-thiabicyclo[2,2,2]octane
1-(4-iodophenyl)-4-n-propyl-2,6-dioxa-7-thiabicyclo[2,2,2]octane
4-t-butyl-1-cyclohexyl-2,6-dioxa-7-thiabicyclo[2,2,2]octane
4-t-butyl-1-cycloheptyl-2,6-dioxa-7-thiabicyclo[2,2,2]octane
1-(4-chlorophenyl)-4-i-butyl-2-oxa-6,7-dithiabicyclo[2,2,2]octane
1-cyclohexyl-4-n-propyl-2,6,7-trithiabicyclo[2,2,2]octane
1-cyclohexyl-8-methyl-4-n-propyl-2,6-dioxa-7-thiabicyclo[2,2,2]octane
1-(4-bromophenyl)-4-i-butyl-8-methyl-2,6-dioxa-7-thiabicyclo[2,2,2]octane
1-(4-bromophenyl)-8-methyl-4-n-propyl-2,6-dioxa-7-thiabicyclo[2,2,2]octane
1-(4-bromophenyl)-4-n-butyl-2,6-dioxa-7-thiabicyclo[2,2,2]octane
1-(4-bromophenyl)-4-n-propyl-2-oxa-6,7-dithiabicyclo[2,2,2]octane.

In a further aspect, the present invention provides a process for the preparation of a compound of the formula (I). The process for the preparation of a compound of the formula (I) may be any method known in the art for preparing analogous compounds, for example when the compound of the formula (I) contains three hetero atoms by the condensation of a compound of the formula (II) with an orthocarboxylate of the formula R$^2$C(OR$^9$)$_3$

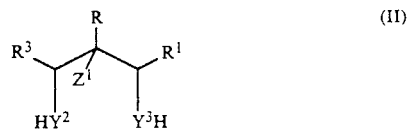

wherein R to R$^3$ are as hereinbefore defined, R$^9$ is C$_{1-4}$ alkyl, phenyl or C$_{7-8}$ aralkyl, Y$^2$ and, Y$^3$ are the same or different and each is oxygen or sulphur and Z$^1$ is a group CH$_2$CH$_2$OH, SH, CH$_2$OH, CH$_2$SH or CHR$^{1x}$NHR$^5$ except that Y$^2$ and Y$^3$ are not both oxygen when Z$^1$ is CH$_2$OH.

This reaction is normally carried out at an elevated temperature, for example between 50° and 200° C., conveniently between 120° and 170° C. in the presence of a base, for example an amine such as triethylamine or of a mineral acid, for example hydrochloric acid or a sulphonic acid derivative such as toluene sulphonic acid or an acid resin. The reaction may conveniently be carried out in the absence of a solvent but a suitable solvent may be added if desired.

The preparation of the compounds of the formula (II) will take place by methods well known to the skilled in the art for preparing compounds of analogous structure. Examples of such methods are shown in the Schemes.

The compounds of the formula (I) wherein Z is CH$_2$CH$_2$ and Y and Y$^1$ are each oxygen may be prepared by the deprotection and cyclisation of a compound of the formula (III):

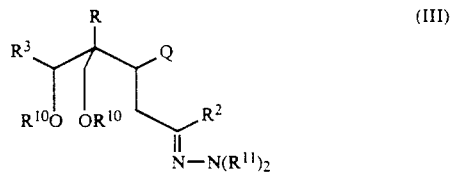

wherein R and R$^2$, are as hereinbefore defined, Q is H, the groups R$^{10}$ are hydroxy protecting groups, and R$^{11}$ is a C$_{1-4}$ alkyl group. Conveniently the groups R$^{10}$ are linked to form, for example, an isopropylidene group but any group that protects the hydroxy groups in the preparation of the compound of the formula (III) and is readily cleaved to permit cyclisation to the compound of the formula (I) is suitable. This cyclisation is conveniently carried out in the presence of a dilute acid that will cleave the protecting group $R^{10}$, for example a dilute mineral acid such as hydrochloric acid. The reaction is suitably carried out at ambient temperature. The preparation of compounds of the formula (III) is illustrated in the Scheme.

The compounds of formula I wherein Z is $CH(OR^8)CH_2$ and Y and $Y^1$ are each oxygen may be prepared by a similar deprotection and cyclisation of a compound of formula III where Q is OH to give initially a compound of formula I having an 8-hydroxy group which may subsequently be converted to a group $OR^8$ e.g. by reaction with $R^8$-halide in the presence of base. Compounds III where Q is OH may be prepared analogously to compounds III where Q is H.

The compounds of the formula (I) wherein Z is $CHR^{1x}NR^5$ and Y and $Y^1$ are each oxygen are preferably prepared by the cyclisation of a compound of the formula (IV) (Scheme 3)

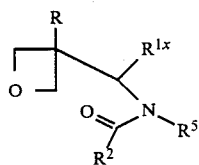

(IV)

wherein R, $R^2$, $R^{1x}$ and $R^5$ are as hereinbefore defined in the presence of an acid catalyst, such as a Lewis Acid. Boron trifluoride etherate is a particularly preferred acid catalyst for this cyclisation which will normally be carried out in an inert solvent, such as a halogenated hydrocarbon, conveniently dichloromethane, at below ambient temperature, for example between $-100°$ and $0°$ C. and conveniently between $-70°$ and $-50°$ C.

The compounds of the formula (IV) may be prepared by the reaction of compounds of the formula (V) and (VI):

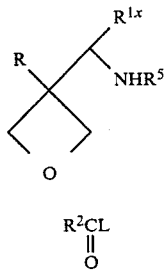

(V)

(VI)

where R, $R^2$, $R^{1x}$ and $R^5$ are as hereinbefore defined and L is leaving group such as halo. This reaction conveniently takes place in an inert solvent in the presence of base at a non-extreme temperature. Halogenated hydrocarbons, such as dichloromethane are particularly suitable solvents, pyridine is a preferred base and the reaction will conveniently be cardried out at between $-50°$ and $100°$ C., preferably at $0°$ C.

The compounds of the formula (V) may in turn be prepared from compounds of the formula (VII) by reaction with an amine ($R^5NH_2$) with sodium cyanoborohydride in a polar solvent, such as an alcohol, for example methanol.

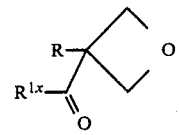

(VII)

The compound of the formula (VII) is prepared by oxidation of the corresponding hydroxy compound, for example by use of oxalyl chloride, dimethylsulphoxide and triethylamine. The hydroxy compound may in turn be prepared from compounds of the formula (II) wherein $R^1$ and $R^3$ are hydrogen, $Y^2$ and $Y^3$ are oxygen and $Z^1$ is $CH_2OH$ by reaction with diethyl carbonate in the presence of a strong base, for example potassium hydroxide in a polar solvent, such as an alcohol, for example ethanol, at an elevated temperature, for example between $50°$ and $100°$ C.

The compounds of Formula (I) may be used to control arthropods such as insect and acarine pests. Thus, the present invention provides a method for the control of arthorpods which comprises administering to the arthorpod or its environment an arthropodicidally effective amount of a compound of the formula (I). The present invention also provides a method for the control and/or eradication of arthropod infestations on animals (including humans) which comprises administering to the animal an effective amount of a compound of the formula (I). The present invention further provides the compounds of the formula (I) for use in human and veterinary medicine for the control of arthropod pests.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapourising mat, wettable powder, granule, aerosol, emulsifiable concentrate, oil suspensions, oil solutions, pressure-pack, impregnated article or pour on formulation. Dip concentrates are not applied per se, but diluted with water and the animals immersed in a dipping bath containing the dip wash. Sprays may be applied by hand or by means of a spray race or arch. The animal; plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules comprise the compound of Formula (I) in intimate admixture with a powdered solid inert carrier for example suitable clays, kaolin, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base. Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammalian host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body.

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%.

The compounds of formula (I) are also of use in the protection and treatment of plant species, in which case an effective insecticidal or acaricidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 Kg/Ha and preferably between 0.01 and 1 Kg/Ha. Typical formulations for agricultural use contain between 0.0001% and 50% of a compound of formula (I) and conventiently betwee 0.1 and 15% by weight of a compound of the formula (I).

Particular crops include cotton, wheat, maize, rice, sorghum, soya, vines, tomatoes, potatoes, fruit trees and spruce.

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Tetranychus urticae Plutella xylostella*, *Culex* spp. and *Blattella germanica*) The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Tribolium, Sitophilus, Diabrotica, Anthonomus or Anthrenus spp.), Lepidoptera (e.g. Ephestia, Plutella, Chilo, Heliothis, Spodoptera or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Aleurodes, Nilopavata, Nephrotetix or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.), Siphonaptera (e.g. Ctenocephalides or Pulex spp.), Thysanura (e.g. Lepisma spp.), Dermaptera (e.g. Forficula spp.) and Pscoptera (e.g. Peripsocus spp.).

Acarine pests include ticks, e.g. members of the genera Boophilus, Rhipicephalus, Amblyomma, Hyalomma, Ixodes, Haemaphysalis, Dermocentor and Anocentor, and mites and manges such as Tetranychus, Psoroptes, Notoedres, Psorergates, Chorioptes and Demodex spp.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1-1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

The following Examples illustrate, in a non-limiting manner, preferred aspects of the invention. All temperatures are in degrees Celsius. When used herein the term ether refers to diethyl ether.

EXAMPLE 1

1-(4-chlorophenyl)-4-ethyl-2,6-dioxabicyclo[2,2,2]octane.

1-(4-chlorophenyl)-4-n-propyl-2,6-dioxabicyclo[2,2,2]octane (i) Methanesulphonyl chloride (15 ml.) was added dropwise to a stirred solution of 2,2-dimethyl-5-ethyl-5-hydroxymethyl-1,3-dioxane $^1$ (33.0 g) in dry pyridine (100 ml.) at 0°. The mixture was stirred for two hours at room temperature and then poured into water. The aqueous mixture was extracted with ether. The ethereal extracts were washed with water, dried over anhydrous magnesium sulphate and evaporated in vacuo. 2,2-Dimethyl-5-ethyl-5-hydroxymethyl-1,3-dioxane methane sulphonate was obtained as a colourless oil (39 g.) which solidified on standing. The compound was used without further purification.

Gas-liquid chromatography (g.l.c.): OV210 at 150° produced one peak.

Nuclear magnetic resonance spectrum (NMR) was as follows: $^1$H (ppm from TMS in CDCl$_3$, integral, number of peaks): 4.40, 2H, s; 3.70, 4H, s; 3.10, 3H, s; 1.50, 8H, m; 0.90, 3H, m.

(ii) A mixture of 2,2-dimethyl-5-ethyl-5-hydroxymethyl-1,3-dioxane methylsulphonate (6.0 g.) and sodium iodide (9.0 g.) in ethyl methyl ketone was refluxed, with stirring, for forty-eight hours. The solvent was removed in vacuo and the resulting oil was poured into water. The aqueous mixture was extracted with ether. The ethereal extracts were washed with 5% aqueous sodium thiosulphate solution and then water. The ethereal extracts were dried over anhydrous magnesium sulphate and then evaporated in vacuo. The residue was purified by column chromatography on silica, eluting with 1:10 ether: hexane. 2,2-Dimethyl-5-ethyl-5-iodomethyl-1,3-dioxane was obtained as a colourless oil (5.0 g.)

Gas-liquid chromatography (g.l.c.): OV210 at 150° produced one peak.

Nuclear magnetic resonance spectrum (NMR) was as follows: $^1$H (ppm from TMS in CDCl$_3$, integral, number of peaks): 3.75, 4H,s; 3.45, 2H,s; 1.20, 8H,m; 0.90, 3H,m, (iii) and (iv) a) n-Butyl-lithium (5.3 ml., 1.6M hexane solution) was added to a stirred solution of 4-chloroacetophenone N,N-dimethylhydrazone (1.5 g., b.pt. 80°-82° 0.05 m.m.) in dry tetrahydrofuran (50 ml.) at −70°, under nitrogen. The mixture was stirred at −70° for thirty minutes. A solution of 2,2-dimethyl-5-ethyl-5-iodomethyl-1,3-dioxane (2.4 g.) in dry tetrahydrofuran (20 ml.) was added to the stirred mixture at −70°. The mixture was allowed to warm up slowly to room temperature. The mixture was stirred at room temperature for twenty-one hours. Water was added and the mixture was extracted with ether. The ether extracts were washed with water, dried over anhydrous magnesium sulphate and evaporated in vacuo.

The residue (2.9 g.) and 2N hydrochloric acid (40 ml.) were stirred at room temperature for twenty-four hours. The aqueous mixture was extracted with ether. The ether extracts were washed with water, dried over anhydrous magnesium sulphate and evaporated in vacuo. The residue was purified by chromatography on silica, eluting with 1:20 ether: hexane. 1-(4-Chlorophenyl)-4-ethyl-2,6-dioxabicyclo[2,2,2]octane was obtained as colourless crystals (0.6 g.) (m.pt. 78°).

Gas-liquid chromatography (g.l.c.): OV210 at 210° produced one peak.

Nuclear magnetic resonance spectrum (NMR) was as follows: $^1$H (p.p.m. from TMS in CDCl$_3$, integral, number of peaks, JH$_z$): 7.40, 2H, d, 8; 7.30, 2H, d, 8; 4.00, 4H, s; 2.20, 2H, m; 1.90, 2H, m; 1.20, 2H, m; 0.90, 3H. m.

Infrared spectrum (1R) (nujol mull): $\nu$1130(S), 1100(m), 1090(m), 1070(m), 1020(s) cm.$^{-1}$ Mass spectrum (MS), chemical ionisation: M+1, 253.

(b) 1-(4-chlorophenyl)-4-n-propyl-2,6-dioxabicyclo[2,2,2]octane (m.pt. 94°) was prepared in an analogous manner by substituting 2,2-dimethyl-5-n-propyl-5-hydroxymethyl-1,3-dioxane 1,1a for 2,2-dimethyl-5-ethyl-5-hydroxymethyl-1,3-dioxane.

Gas-liquid chromatography (g.l.c.): OV210 at 185° produced one peak.

Nuclear magnetic resonance spectrum (NMR) was as follows: $^1$H (ppm from TMS in CDCl$_3$, integral, number of peaks): 7.10, 4H, m; 3.80, 4H, s; 1.90, 2H, m; 1.70, 2H, m; 1.00, 4H, m; 0.80, 3H, m. Infrared spectrum (1R) (nujol mull): 1130 (s), 1080 (m), 1020 (S). Mass spectrum (MS), chemical ionisation: M+1.267.

EXAMPLE 2

1-(4-Bromophenyl)-4-ethyl-2,6-dioxa-7-thiabicyclo[2,2,2]octane.

1-(4-Bromophenyl)-4-n-propyl-2,6-dioxa-7-thiabicyclo[2,2,2]octane (i) Sodium hydride (340 mg., 50% dispersion in paraffin oil) was added carefully to a stirred solution of thiolacetic acid (500 mg.) in dry dimethylformamide (100 ml.) at 20°. After 30 minutes 2,2-dimethyl-5-ethyl-5-iodomethyl-1,3-dioxane (2.0 g.) was added. The mixture was refluxed with stirring for 2 hours. The mixture was cooled and poured into water. The aqueous mixture was extracted with ether. The ethereal extracts were washed with water and dried over anhydrous magnesium sulphate. The solution was evaporated in vacuo. The residue was purified by column chromatography on silica, eluting with 1:4 ether:hexane. 5-Acetylthiomethyl-5-ethyl-2,2-dimethyl-1,3-dioxane was obtained as a pale yellow oil (1.5 g.)

Gas-liquid chromatography (g.l.c.): OV210 at 150° produced one peak.

Nuclear magnetic resonance spectrum (NMR) was as follows: $^1H$ (p.p.m from TMS in $CDCl_3$, integral, number of peaks JHz): 3.70, 4H, s; 3.20, 2H, s; 2.45, 3H, s; 1.50, 8H m; 0.90, 3H, m (ii) and (iii) 5-Acetylthiomethyl-5-ethyl-2,2-dimethyl-1,3-dioxane (2.0 g.) was stirred at 20°, in 10% aqueous sodium hydroxide solution (2.0 ml.) in methanol (20 ml.), for 24 hours under nitrogen. The mixture was neutralized with concentrated hydrochloric acid (0.5 ml.). Dowex 50×8-200 ion exchange resin ($H^+$ form) (1.0 g.) was added and the mixture was refluxed with stirring, under nitrogen, for 4 hours. The mixture was filtered and the filtrate was evaporated in vacuo. Toluene was added to the residue and the mixture was evaporated in vacuo. 2,2-Di-(hydroxymethyl)-butanethiol was obtained as a colourless oil and was used without further purification (1.0 g.)

(iv)a) 2,2-Di-(hydroxymethyl)-butanethiol (0.5 g.), trimethyl 4-bromo-orthobenzoate [2] (1.0 g.) and triethylamine (0.1 ml.) were heated at 130°, under a current of nitrogen, for 45 minutes. The volatile components were removed in vacuo (2.00 mm.), at 140°. The residue was purified by chromatography on alumina (alumina Woelm TSC) eluting with 1:6 dichloromethane: hexane, saturated with ammonia. 1-(4-Bromophenyl)-4-ethyl-2,6-dioxa-7-thiabicyclo[2,2,2]octane was obtained as colourless crystals (80 mg.).

Gas-liquid chromatography (g.l.c.): OV210 at 200° produced one peak.

Nuclear magnetic resonance spectrum (NMR) was as follows: $^1H$ (ppm from TMS in $CDCl_3$, integral, number of peaks): 7.50, 4H, s; 4.20, 4H, m; 3.15, 2H, s; 1.40, 2H, m; 1.00, 3H, m.

Infrared spectrum (IR) (nujol mull): 1090(s), 1035(m), 1022(w)

Mass spectrum (MS), chemical ionisation: M+1 315, 317

(iv)b) Using a method analogous to that described in (iv)(a) above 2,2-di-(hydroxymethyl)-pentan-1-thiol and trimethyl 4-bromo-orthobenzoate were reacted together to give 1-(4-bromophenyl)-4-n-propyl-2,6-dioxa-7-thiabicyclo[2,2,2]octane.

Gas-liquid chromatography (glc): OV 210 at 200° produced one peak.

Nuclear magnetic resonance spectrum (NMR) was as follows: $^1H$ (ppm from TMS in $CDCl_3$, integral, number of peaks): 7.50, 4H, s; 4.20, 4H, m; 3.20, 2H, m; 1.40, 4H, m; 1.00, 3H, m.

Infrared spectrum (IR) (nujol mull): 1080 (s), 1040 (s), 1020 (m).

Mass spectrum (MS), chemical ionisation: M+1 329, 331

EXAMPLE 3

1-Cyclohexyl-5-n-propyl-2,7,8-trioxabicyclo[3,2,2]nonane.

(i) Sodium hydride (7.5 g., 80% dispersion in oil) was added to a stirred solution of diethyl n-propylmalonate (52 g.) in dry benzene (200 ml.) at room temperature. The mixture was then refluxed, with stirring for 1 hour. The mixture was cooled and ethyl bromoacetate (42 g.) was added dropwise. The reaction mixture was refluxed with stirring for 3 hours. The reaction mixture was cooled and poured into water and the aqueous mixture was extracted into ether. The ether extracts were washed with water, dried over anhydrous magnesium sulphate and the solvent was removed in vacuo.

Distillation gave diethyl 2-ethoxycarbonyl-2-n-propylsuccinate (58 g.) a colourless oil (b.pt. 130°–6° 2.6 mm.)

Gas-liquid chromatography (g.l.c.): OV210 at 150° produced one peak.

Nuclear magnetic resonance spectrum (NMR) was as follows: $^1H$ (p.p.m. from TMS in $CDCl_3$, integral, number of peaks, $JH_z$): 4.25, 6H, m; 3.00, 2H, s; 2.00, 2H, m; 1.50–0.80, 14H, m.

(ii) Diethyl 2-ethoxycarbonyl-2-n-propyl-succinate (55.8 g) in dry ether (50 ml.) was added slowly to a stirred suspension of lithium aluminium hydride (14.7 g.) in dry ether (150 ml.) at 0°, under a current of nitrogen. The mixture was stirred at room temperature for three hours and then refluxed, with stirring for four hours. A solution of potassium hydroxide (30.0 g.), potassium dihydrogen phosphate (22.0 g.) and potassium monohydrogen phosphate (22.0 g.) in water (200 ml.) was added to the cooled reaction mixture. The pH was adjusted to 5.0 with glacial acetic acid. The solid was removed by filtration and washed with water (40 ml.) The combined filtrates and washings were evaporated in vacuo. The residue was washed with acetone (3×100 ml). The acetone washings were evaporated in vacuo. The residue was washed with chloroform (3×100 ml.) and the washings were evaporated in vacuo, Toluene was added and the residue was evaporated in vacuo. 3,3-Di-(hydroxymethyl)-hexan-1-ol was obtained as a colourless oil and was used without further purification.

(iii) From 3,3-Di-(hydroxymethyl)-hexan-1-ol (750 mg.) and trimethyl orthocyclohexyl-carboxylate [3] (1.0 g), using the method described in example 2,1-Cyclohexyl-5-n-propyl-2,7,8-trioxabicyclo[3,2,2]nonane (50 mg.), a colourless oil, was obtained.

Gas-liquid chromatography (g.l.c.): OV210 at 190° produced one peak.

Nuclear magnetic resonance spectrum (NMR) was as follows: $^1H$ (ppm from TMS in $CDCl_3$, integral, number of peaks): 3.80, 6H, m; 2.00–0.80, 20H, m. Infrared spectrum (1R) (liquid film): 1114(s), 1070(s), 1040(s), 1010(m) $cm^{-1}$ Mass spectrum (MS), chemical ionisation: M+1, 255

EXAMPLE 4

4-t-Butyl-1-(4-chlorophenyl)-2,6-dioxabicyclo[2,2,2]octane

A mixture of cyclohexanone (150 ml.), 5-t-butyl-2,2-dimethyl-5-hydroxymethyl-1,3-dioxane methanesulphonate (17.5 g.) (see synthesis of 2,2-dimethyl-5-ethyl-5-hydroxymethyl-1,3-dioxane methanesulphonate and ref. 4) and sodium iodide (12 g.) was refluxed, with stirring, for 24 hours. The solvent was removed in vacuo and the resulting oil was poured into water. The aqueous mixture was extracted with diethyl ether. The ethereal extracts were washed with 5% aqueous sodium thiosulphate solution and then water. The ethereal extracts were dried over anhydrous magnesium sulphate and then evaporated in vacuo. The residue was purified by column chromatography on silica, eluting with hexane. 3-t-Butyl-3-iodomethyl-(1,5-dioxaspiro[5,5]undecane) was obtained as a colourless oil (14 g.) Gas-liquid chromatography (g.l.c.): OV210 at 185° produced one peak.

Nuclear magnetic resonance spectrum (NMR) was as follows: $^1H$ (ppm from TMS in $CDCl_3$, integral, number of peaks, $J_{Hz}$): 3.80, 2H, d, 10; 3.50, 2H, d, 10; 3.40, 2H, S; 1.50, 10H, m; 0.90, 9H, S.

A mixture of 3-t-butyl-3-iodomethyl-(1,5-dioxaspiro[5,5]undecane) (3.5 g.), p-toluenesulphonic acid (0.5 g.) and acetone (200 ml.) was refluxed for 36 hours. The mixture was cooled and sodium hydrogen carbonate (2.0 g.) was added. The solvent was removed in vacuo and the resulting oil was poured into water. The aqueous mixture was extracted with diethyl ether. The ethereal extracts were washed with water, dried over anhydrous magnesium sulphate and then evaporated in vacuo. 5-t-Butyl-2,2-dimethyl-5-iodomethyl-1,3-dioxane was obtained as a colourless oil (2.3 g.) and was used without further purification.

Gas-liquid chromatography (g.l.c.): OV210 at 170° produced one peak.

Nuclear magnetic resonance spectrum (NMR) was as follows: $^1H$ (ppm from TMS in $CDCl_3$, integral, number of peaks, $J_{Hz}$): 3.70, 2H, d, 10; 3.50, 2H, d, 10; 3.30, 2H, s; 1.20, 6H, s; 0.80, 9H, s.

4-t-Butyl-1-(4-chlorophenyl)-2,6-dioxa-bicyclo[2,2,2]octane was prepared from 5-t-butyl-2,2-dimethyl-5-iodomethyl-1,3-dioxane using the method described for the synthesis of 1-(4-chlorophenyl)-4-ethyl-2,6-dioxabicyclo[2,2,2]octane.

Physical Data: - Gas-liquid chromatography (g.l.c.): OV210 at 200° produced one peak. Melting Point 155°

Nuclear magnetic resonance spectrum (NMR) was as follows: $^1H$ (ppm from TMS in $CDCl_3$, integral, number of peaks): 7.25, 4H, m; 4.10, 4H, m; 2.10, 2H, m; 2.00, 2H, m; 1.00, 9H, s.

Infrared spectrum (1R) (nujol mull): 1130(s), 1100(s), 1015(s)

Mass spectrum (MS), chemical ionisation: M+1 281.

EXAMPLE 5

1-(4-Chlorophenyl)-8-hydroxy-4-n-propyl-2,6-dioxabicyclo[2,2,2]octane, and
1-(4-Chlorophenyl)-4-ethyl-8-hydroxy-2,6-dioxabicyclo[2,2,2]octane 2,2-Dimethyl-5-ethyl-5-hydroxymethyl-1,3-dioxane (33 g.) was added to a stirred suspension of pyridinium chlorochromate (122.6 g) and anhydrous sodium acetate (7.8 g.) in dry dichloromethane (200 ml.), at 0°, under a current of nitrogen. The mixture was stirred at room temperature for six hours. The mixture was diluted with dry ether (500 ml) and the organic solution was decanted off. The oily residue was treated with ether and the combined extracts were evaporated in vacuo. The residue was purified by chromatography on silica, eluting with ether: hexane 1:3. 2,2-Dimethyl-5-ethyl-5-formyl-1,3-dioxane (30 g.) was obtained as a colourless oil.

Gas-liquid chromatography (g.l.c.): OV210 at 130° produced one peak.

Nuclear magnetic resonance spectrum (NMR) was as follows: $^1H$ (ppm from TMS in $CDCl_3$, integral, number of peaks, $J_{Hz}$): 9.6, 1H, s; 4.2, 2H, d, 12; 3.8, 2H, d, 12; 1.4, 8H, m; 0.85, 3H, t, 6.

2,2-Dimethyl-5-formyl-5-n-propyl-1,3-dioxane was prepared in an analogous manner from 2,2-dimethyl 5-hydroxymethyl-5-n-propyl-1,3-dioxane.

n-Butyl-lithium (29 ml, 1.6M hexane solution) was added to a stirred solution of 4-chloro-acetophenone N,N-dimethylhydrazone (9.0 g.) in dry tetrahydrofuran (100 mls), at −70°, under nitrogen. The mixture was stirred at −70° for 30 minutes. A solution of 2,2-dimethyl-5-formyl-5-n-propyl-1,3-dioxane (9.5 g.) in dry tetrahydrofuran (20 mls), at −70° was added. The mixture was allowed to warm up slowly to room temperature and then stirred at room temperature for 5 days.

Water was added and the mixture was extracted with diethyl ether. The ethereal extracts were washed with water, dried over anhydrous magnesium sulphate and evaporated in vacuo.

The residue (16 g.) and 2N hydrochloric acid (50 mls) were stirred at room temperature for 24 hours.

The aqueous mixture was extracted with diethyl ether. The ethereal extracts were washed with water, dried over anhydrous magnesium sulphate and evaporated in vacuo. The residue was purified by chromatography on silica, eluting with 1:2 ether:hexane. 1-(4-Chlorophenyl)-8-hydroxy-4-n-propyl-2,6-dioxabicyclo[2,2,2]octane was obtained as a waxy solid (3.5 g.)

Nuclear magnetic resonance spectrum (NMR) was as follows: $^1H$ (ppm from TMS in $CDCl_3$, integral, number of peaks): 7.30, 4H, m; 3.90, 5H, m; 3.00–1.70 3H, m; 1.40–0.70, 7H, m.

Infrared spectrum (1R) (nujol mull): 3470(s and br), 1130(m), 1100(s), 1030(s).

Mass spectrum (MS), chemical ionisation: M+1 283

1-(4-Chlorophenyl)-4-ethyl-8-hydroxy-2,6-dioxabicyclo[2,2,2]octane was prepared in a similar manner.

Physical Data

Melting Point 97°

Nuclear magnetic resonance spectrum (NMR) was as follows: $^1H$ (ppm from TMS in $CDCl_3$, integral, number of peaks): 7.35, 4H, m; 4.00, 5H, m; 3.00–1.70, 3H, m; 1.30, 2H, m; 0.90, 3H, m.

Infrared spectrum (1R) (nujol mull): 3450 (s and br), 1130(m), 1100(s), 1080(s), 1020(m).

Mass spectrum (MS), chemical ionisation: M+1 269

EXAMPLE 6

1-(4-Chlorophenyl)-8-methoxy-4-n-propyl-2,6-dioxabicyclo[2,2,2]octane n-Butyl-lithium (440 μl, 1.6M hexane solution) was added to a stirred solution of 1-(4-chlorophenyl)-8-hydroxy-4-n-propyl-2,6-dioxabicyclo[2,2,2]octane (200 mg.) in dry tetrahydrofuran (10 mls), under a current of nitrogen, at 0°. The mixture was stirred for 30 minutes and methyl iodide (200 μl) was added. The mixture was stirred at room temperature, under a current of nitrogen, for 2 days. Water was added and the aqueous mixture was extracted with diethyl ether. The ethereal extracts were washed with water, dried over anhydrous magnesium sulphate and evaporated in vacuo. The residue was purified by column chromatography on silica, eluting with 1:10 ether:hexane.

1-(4-Chlorophenyl)-8-methoxy-4-n-propyl-2,6-dioxabicyclo[2,2,2]octane was obtained as a colourless solid (66 mg.)

Nuclear magnetic resonance spectrum (NMR) was as follows: $^1$H (ppm from TMS in CDCl$_3$, integral, number of peaks): 7.30, 4H, m; 4.40–3.40, 5H, m; 3.30, 3H, s; 2.80–1.80, 2H, m; 1.50–0.80, 7H, m.

Mass spectrum (MS), chemical ionisation: M+1 297.

EXAMPLE 7

8-Acetoxy-1-(4-chlorophenyl)-4-n-propyl-2,6-dioxabicyclo[2,2,2]octane

A solution of 1-(4-chlorophenyl)-8-hydroxy-4-n-propyl-2,6-dioxabicyclo[2,2,2]octane (500 mg.) and triethylamine (296 µl) in dry ether (20 mls) was stirred at 0°.

Acetyl chloride (125 µl) was added and the mixture was stirred at room temperature for 24 hours. The mixture was poured into water and the aqueous mixture was extracted with diethyl ether. The ethereal extracts was washed with water, dried over anhydrous magnesium sulphate and the solution was evaporated in vacuo. The residue was purified by column chromatography on silica, eluting with 1:6 diethyl ether:hexane.

8-Acetoxy-1-(4-chlorophenyl)-4-n-propyl-2,6-dioxabicyclo[2,2,2]octane was obtained as a waxy solid (100 mg.).

Nuclear magnetic resonance spectrum (NMR) was as follows: $^1$H (ppm from TMS in CDCl$_3$, integral, number of peaks):

7.40, 4H, m; 5.20, 1H, d, 8; 4.40–3.80, 4H, m; 3.00–2.50, 2H, m; 2.20, 3H, s; 1.40–0.8, 7H, m.

Mass spectrum (MS), chemical ionisation: M+1 325.

EXAMPLE 8

1-(4-Chlorophenyl)-8-oxo-4-n-propyl-2,6-dioxabicyclo[2,2,2]octane.

1-(4-Chlorophenyl)-8-hydroxy-4-n-propyl-2,6-dioxabicyclo[2,2,2]octane (500 mg.) was added to a stirred suspension of pyridinium chlorochromate (955 mg.) and anhydrous sodium acetate (270 mg.) in dry dichloromethane (20 mls.), at 0°, under a current of nitrogen. The mixture was stirred at room temperature for six hours. The mixture was diluted with dry diethyl ether (50 mls.) and the organic solution was decanted off. The oily residue was treated with diethyl ether and the combined extracts were evaporated in vacuo.

The residue was purified by column chromatography on silica, eluting with 1:3 diethyl ether:hexane.

1-(4-Chlorophenyl)-8-oxo-4-n-propyl-2,6-dioxabicyclo[2,2,2]octane was obtained as a colourless solid (240 mg.) (m.pt. 96°).

Gas-liquid chromatography (g.l.c.):
OV210 at 185° produced one peak.

Nuclear magnetic resonance spectrum (NMR) was as follows: $^1$H (ppm from TMS in CDCl$_3$, integral, number of peaks): 7.40, 4H, m; 4.20, 4H, s; 3.00, 2H, s; 1.50, 4H, m; 1.00, 3H, m.

Infrared spectrum (IR) (nujol mull): 1750(s), 1130(m), 1100(m), 1030,(m), 1010(m).

Mass spectrum (MS), chemical ionisation: M+1 281

EXAMPLE 9

1-(4-Chlorophenyl)-4-n-propyl-2,6-dioxabicyclo[2,2,2]oct-8-yl methanesulphonate

Methanesulphonyl chloride (164 µl) was added to a stirred solution of 1-(4-chlorophenyl)-8-hydroxy-4-n-propyl-2,6-dioxabicyclo[2,2,2]octane (500 mg.) in dry pyridine (2.0 ml.). The mixture was stirred at room temperature for 6 hours. The mixture was poured into water and the aqueous mixture was extracted with diethyl ether. The ethereal extracts were washed with 1N hydrochloric acid solution. The ethereal extracts were then washed with saturated aqueous sodium hydrogen carbonate solution. The ethereal extracts were washed with water, dried over anhydrous magnesium sulphate and evaporated in vacuo.

The residue was washed with diethyl ether and the remaining solid was dried in air.

1-(4-Chlorophenyl)-4-n-propyl-2,6-dioxabicyclo[2,2,2]oct-8-ylmethane sulphonate was obtained as a colourless solid (220 mg.)

Nuclear magnetic resonance spectrum (NMR) was as follows: $^1$H (ppm from TMS in CDCl$_3$, integral, number of peaks): 7.40, 4H, m; 5.10, 1H, d, 6; 4.30–3.8, 4H, m; 3.10, 3H, s; 3.00–2.40, 2H, m; 1.50, 4H, m; 1.00, 3H, m.

Mass spectrum (MS), chemical ionisation: M+1 361

EXAMPLE 10

1-(4-Bromophenyl)-4-isobutyl-2,6-dioxa-7-thiabicyclo[2,2,2]octane (1) Diethyl isobutylmalonate (22.0 g.) was added to a stirred suspension of sodium hydride (4.8 g. 50% dispersion in oil) in dry toluene (200 ml.), under nitrogen. The mixture was stirred at 80° for one hour. The mixture was cooled and benzyl chloromethyl thioether $^5$(16.0 g.) in dry toluene (50 ml.) was added and the mixture was stirred at 80° for two hours. The mixture was cooled and poured into water. The aqueous mixture was extracted into diethyl ether. The ether extracts were washed with water, dried over anhydrous magnesium sulphate and evaporated in vacuo. Diethyl 2-benzylthiomethyl-2-isobutylmalonate (32.0 g.) was obtained as a yellow oil and was used without further purification.

(ii) Diethyl 2-benzylthiomethyl-2-isobutylmalonate (32.0 g.) in dry diethyl ether (60 ml.) was added to a stirred suspension of lithium aluminium hydride (7.0 g.) in dry diethyl ether (400 ml.), at 0°, under nitrogen. The mixture was stirred at room temperature for three hours and then refluxed with stirring for a further three hours. The mixture was cooled and 10% aqueous sodium hydroxide solution (25 ml.) was added very carefully. The mixture was filtered and the solid was washed with ether. The filtrates were dried over anhydrous magnesium sulphate and evaporated in vacuo. 2-Benzylthiomethyl-2-isobutyl-propan-1,3-diol was obtained as a colourless solid (20 g.) and was used without further purification.

(iii) 2-Benzylthiomethyl-2-isobutyl-propan-1,3-diol (7.0 g.) in dry diethyl ether (150 ml.) was added to liquid ammonia (150 ml.) at −70°. Sodium (1.8 g.) was added to the stirred solution. Stirring was maintained at −70°, for one hour. The mixture was then allowed to warm up to −30° and solid ammonium chloride (10 g.) was added cautiously The ammonia was removed from the reaction mixture under a current of nitrogen. The residue was washed with dry dichloromethane and the filtrates were evaporated in vacuo. 2,2-Di-hydroxymethyl-4-methyl-pentan-1-thiol (2.5 g.) was obtained as a colourless smelly oil and was used without further purification.

(iv) From 2,2-di-hydroxymethyl-4-methyl-pentan-1-thiol (1.2 g.) and trimethyl 4-bromo-orthobenzoate using the method described in Example 2 but using one drop of conc. hydrochloric acid as a catalyst in the place of triethylamine,1-(4-bromophenyl)-4-isobutyl-2,6-dioxa-7-thiabicyclo[2,2,2]octane, a colourless solid, was obtained (90 mg.) after recrystallisation from hexane.

In an analogous manner, from 2,2-di-hydroxymethyl-3-methyl-butan-1-thiol or 2,2-di-hydroxymethyl-3-methyl-pentan-1-thiol and trimethyl 4-bromoorthobenzoate or trimethyl 4-chloro-orthobenzoate or trimethyl orthocyclohexyl-carboxylate the following compounds were prepared:

-1-(4-Bromophenyl)-4-i-propyl-2,6-dioxa-7-thiabicyclo[2,2,2]octane.
1-(4-Bromophenyl)-4-s-butyl-2,6-dioxa-7-thiabicyclo[2,2,2]octane
1-(4-Chlorophenyl)-4-s-butyl-2,6-dioxa-7-thiabicyclo[2,2,2]octane 4-s-Butyl-1-cyclohexyl-2,6-dioxa-7-thiabicyclo[2,2,2]octane 3,3-Di-hydroxymethyl-hexan-2-thiol and 3,3-di-hydroxymethyl-5-methylhexan-2-thiol were prepared by an analogous manner from diethyl n-propylmalonate and diethyl isobutylmalonate respectively and benzyl 1-chloroethyl thioether[6].

3,3-di-hydroxymethyl-hexan-2-thiol or 3,3-di-hydroxymethyl-5-methylhexan-2-thiol were reacted with trimethyl 4-bromo-orthobenzoate[2] or trimethyl orthocyclohexylcarboxylate[3] in an analogous manner to give the following compounds:

-1-(4-Bromophenyl)-8-methyl-4-n-propyl-2,6-dioxa-7-thiabicyclo[2,2,2]octane
1-Cyclohexyl-8-methyl-4-n-propyl-2,6-dioxa-7-thiabicyclo[2,2,2]octane
1-(4-Bromophenyl)-4-i-butyl-8-methyl-2,6-dioxa-7-thiabicyclo[2,2,2]octane.

2,2-di-hydroxymethyl-hexan-1-thiol was prepared in an analogous manner to 2,2-di-hydroxymethyl-4-methyl-pentan-1-thiol starting from diethyl n-butylmalonate.

1-(4-Bromophenyl)-4-n-butyl-2,6-dioxa-7-thiabicyclo[2,2,2]octane (m.pt. 110°-112°) was prepared from trimethyl 4-bromo-orthobenzoate[2] and 2,2-di-hydroxymethyl-hexan-1-thiol in an analogous manner to the compounds described above.

EXAMPLE 11

1-(4-Bromophenyl)-4-t-butyl-2,6-dioxa-7-thiabicyclo[2,2,2]octane (i) Sodium hydride (1.25 g., 50% dispersion in oil) was added to a stirred solution of benzyl mercaptan (3.2 ml.) in dry dimethylformamide (75 ml) at 0°, under a current of nitrogen. Stirring was maintained for 30 minutes. 5-t-Butyl-2,2-dimethyl-5-hydroxymethyl-1,3-dioxane methanesulphonate (7.5 g.) was added and the mixture was maintained at 130°, with stirring for 7 hours. The reaction mixture was cooled and poured into water. The aqueous mixture was extracted with diethyl ether. The ethereal extracts were washed with water, dried over anhydrous magnesium sulphate and then evaporated in vacuo. 5-Benzylthiomethyl-5-t-butyl-2,2-dimethyl-1,3-dioxane (7.0 g.) was obtained as a mobile oil and was used without further purification.

(ii) 5-Benzylthiomethyl-5-t-butyl-2,2-dimethyl-1,3-dioxane (7.0 g.) and Dowex 50×8-200 ion exchange resin (H+ form) (0.6 g.) in methanol (100 ml.) containing water (10 ml.) was refluxed, with stirring, for 3 hours. The mixture was filtered and the filtrate was evaporated in vacuo. 2-Benzylthiomethyl-2-hydroxymethyl-3,3-dimethyl-butan-1-ol was obtained as a colourless oil (5.0 g.) and was used without further purification.

(iii) 2-Benzylthiomethyl-2-hydroxymethyl-3,3-dimethyl-butan-1-ol (5.0 g.) in dry diethyl ether was added to liquid ammonia (250 ml.) at −70°. Sodium (2.0 g.) was added to the stirred solution and stirring was continued for one hour at −70°. The mixture was allowed to warm up to room temperature, under a current of nitrogen. Solid ammonium chloride (20.0 g.) was added. The mixture was filtered and the solid was washed with methanol (100 ml.). The filtrates were evaporated in vacuo. The resulting solid was washed with chloroform (500 ml.). The washings were evaporated in vacuo.

2,2-di-hydroxymethyl-3,3-dimethyl-butan-1-thiol was obtained as a crystalline solid (4.0 g.)

Nuclear magnetic resonance spectrum (NMR) was as follows: $^1H$ (p.p.m. from TMS in $CDCl_3$, integral, number of peaks, $J_{Hz}$): 4.00, 4H, s; 3.20–2.90, 4H, m; 1.90, 1H, t, 7:1.10, 9H, s.

Mass spectrum (MS), chemical ionisation: m+1, 179

From 2,2-di-hydroxymethyl-3,3-dimethyl-butan-1-thiol and trimethyl 4-bromo-orthobenzoate, trimethyl 4-chloro-orthobenzoate, trimethyl orthocyclohexylcarboxylate and trimethyl ortho-cycloheptylcarboxylate in the manner described previously, the following compounds were prepared:

-1-(4-Bromophenyl)-4-t-butyl-2,6-dioxa-7-thiabicyclo[2,2,2]octane
4-t-Butyl-1-(4-chlorophenyl)-2,6-dioxa-7-thiabicyclo[2,2,2]octane
4-t-Butyl-1-cyclohexyl-2,6-dioxa-7-thiabicyclo[2,2,2]octane
4-t-Butyl-1-cycloheptyl-2,6-dioxa-7-thiabicyclo[2,2,2]octane

EXAMPLE 12

1-(4-Chlorophenyl)-4-isobutyl-2-oxa-6,7-dithiabicyclo[2,2,2]octane (i) Methanesulphonyl chloride (26.0 ml.) was added dropwise to a stirred solution of 2-benzyloxymethyl-2-hydroxymethyl-4-methyl-pentan-1-ol (prepared from diethyl isobutylmalonate in a manner analogous to that described for the synthesis of 2-benzyloxymethyl-2-cyclohexyl-propan-1,3-diol (Example 16)). (41.6 g.) and dry pyridine (30 ml) in dry diethyl ether (300 ml) at 0°. The mixture was stirred at room temperature for 24 hours and the mixture was poured into water. The aqueous mixture was extracted with diethyl ether. The ethereal extracts were washed with 1N hydrochloric acid solution, saturated sodium hydrogen carbonate solution and then water. The ethereal extracts were dried over anhydrous magnesium sulphate and evaporated in vacuo.

The residue was purified by chromatography on silica, eluting with 1:1 diethyl ether:hexane. 2-Benzyloxymethyl 2-hydroxymethyl-4-methylpentan-1-ol dimethanesulphonate was obtained as an oil (23 g.).

Nuclear magnetic resonance spectrum (NMR) was as follows: $^1H$ (p.p.m. from TMS in $CDCl_3$, integral, number of peaks, $J_{Hz}$): -7.40, 5H, s; 4.60, 2H, s; 4.30, 4H, s; 3.60, 2H, s; 3.10, 6H, s; 2.20–1.00, 9H, m.

Mass spectrum (MS), chemical ionisation: m+1, 409.

(ii) 1-Benzyloxy-2,2-di-benzylthiomethyl-4-methyl-pentane was prepared from 2-benzyloxymethyl-2-hydroxymethyl-4-methyl-pentan-1-ol dimethanesulphonate in a manner analogous to that described for the synthesis of 5-benzylthiomethyl-5-t-butyl-2,2-dimethyl-1,3-dioxane.

Nuclear magnetic resonance spectrum (NMR) was as follows: $^1$H (p.p.m. -from TMS in CDCl$_3$, integral, number of peaks, J$_{Hz}$): -7.10, 15H, m; 4.40, 2H, s; 3.60, 4H, s; 3.30, 2H, s; 2.50, 4H, s; 1.80–0.80, 9H.

Mass spectrum (MS), chemical ionisation: m+1, 465

2-i-Butyl-2-hydroxymethyl-propan-1,3-dithiol was prepared from 1-benzyloxy-2,2-di-benzylthiomethyl-4-methyl-pentane in a manner analogous to that described for the sysnthesis of 2,2-di-hydroxymethyl-3,3-dimethyl-butan-1-thiol.

1-(4-Chlorophenyl)-4-isobutyl-2-oxa-6,7-di-thia-bicyclo[2,2,2]octane was prepared from 2-i-butyl-2-hydroxymethyl-propan-1,3-dithiol and trimethyl 4-chloro-orthobenzoate in the manner described previously.

Nuclear magnetic resonance spectrum (NMR) was as follows: $^1$H (p.p.m. from TMS in CDCl$_3$, integral, number of peaks, J$_{Hz}$); -7.65, 2H, d, 7; 7.45, 2H, d, 7; 4.25, 2H, s; 3.10, 4H, m; 1.75, 1H, m; 1.30, 2H, d, 6; 1.00, 6H, d, 6.

Mass spectrum (MS), chemical ionisation: m+1, 315.

2-hydroxymethyl-2-n-propyl-propan-1,3-dithiol was prepared in an analogous manner to 2-i-butyl-2-hydroxymethyl-propan-1,3-dithiol starting from 2-benzyloxymethyl-2-n-propyl-propan-1,3-diol.

1-(4-Bromophenyl)-4-n-propyl-2-oxa-6,7-dithiabicyclo[2,2,2]octane was prepared from trimethyl 4-bromo-orthobenzoate and 2-hydroxymethyl-2-n-propyl-propan-1,3-dithiol.

Nuclear magnetic resonance spectrum (NMR) was as follows: $^1$H (p.p.m. from TMS in CDCl$_3$, integral, number of peaks, J$_{Hz}$); 7.50, 4H, m; 4.20, 2H, m; 3.10, 4H, m; 1.35, 4H, m; 0.95, 3H, m.

Mass spectrum (MS), chemical ionisation: m+1, 345, 347

EXAMPLE 13

1-Cyclohexyl-4-n-propyl-2,6,7-tri-thia-bicyclo[2,2,2]octane

Starting from 2-hydroxymethyl-2-n-propyl-propan-1,3-diol and using a reaction scheme analogous to that described in example 12 1-cyclohexyl-4-n-propyl-2,6,7-tri-thia-bicyclo[2,2,2]octane (clear oil) was prepared.

Nuclear magnetic resonance spectrum (NMR) was as follows: $^1$H (p.p.m. from TMS in CDCl$_3$, integral, number of peaks, J$_{Hz}$): 3.00, 6H, s; 2.00–0.80, 18H, m.

Mass spectrum (MS), chemical ionisation: m+1, 289.

EXAMPLE 14

1-(4-Bromophenyl)-3-methyl-4-n-propyl-2,6-dioxa-7-thiabicyclo[2,2,2]octane (i) 2-Benzylthiomethyl-2-n-propyl-propan-1,3-diol (14.2 g.) (prepared from diethyl n-propylmalonate in a manner analogous to that described for the synthesis of 2-benzylthiomethyl-2-isobutyl-propan-1,3-diol (Example 10)) in dry tetrahydrofuran (100 ml.) was stirred at 0°, under a current of nitrogen. Sodium hydride (2.7 g, 50% dispersion in oil) was added carefully and the mixture was stirred at 20° for 1 hour. Benzyl bromide (9.6 g.) was added carefully and the reaction mixture was refluxed, with stirring for 12 hours. The mixture was cooled and poured into water. The aqueous mixture was extracted with diethyl ether. The ethereal extracts were washed with water, dried over anhydrous magnesium sulphate and then evaporated in vacuo.

2-Benzyloxymethyl-2-benzylthiomethyl-pentan-1-ol was obtained as a pale yellow oil (22 g.) and was used without further purification.

(ii) 2-Benzyloxymethyl-2-benzylthiomethyl-pentan-1-ol (5 g.) was added to a stirred suspension of pyridinium chlorochromate (5 g.) and anhydrous sodium acetate (3.0 g.) in dry dichloromethane (20 ml.) at 0°, under a current of nitrogen. The mixture was stirred at room temperature for 3 hours. The mixture was diluted with diethyl ether (100 ml.) and the organic solution was decanted off. The oily residue was treated with ether and the combined extracts were evaporated in vacuo. The residue was chromatographed on silica eluting with ethyl acetate:hexane, 1:10. 2-Benzyloxymethyl-2-benzylthiomethyl-pentanal was obtained as a colourless oil (1.9 g.).

Nuclear magnetic resonance spectrum (NMR) was as follows: $^1$H (p.p.m. from TMS in CDCl$_3$, integral, number of peaks): -9.50, 1H, s; 7.30, 10H, s; 4.50, 2H, s; 3.80, 2H, s; 3.65, 2H, s; 2.95, 2H, s; 1.80–0.80, 7H, m.

Infrared spectrum (IR) (liquid film): $\nu$ 1735 cm$^{-1}$

Mass spectrum (MS), chemical ionisation: m+1, 343

(iii) Methyl magnesium iodide (4.0 ml, 3M solution in ether) was added to a solution of 2-benzyloxymethyl-2-benzylthiomethyl-pentanal (2.6 g.) in dry diethyl ether (50 ml.) at 0°. The mixture was refluxed, with stirring for 2 hours. The mixture was cooled and poured into 1N hydrochloric acid in ice. The aqueous mixture was extracted with diethyl ether. The ethereal extracts were washed with water, dried over anhydrous magnesium sulphate and evaporated in vacuo. The residue was chromatographed on silica, eluting with diethyl ether. 3-Benzyloxymethyl-3-benzylthiomethylhexan-2-ol was obtained as a colourless oil (0.7 g.).

Gas-liquid chromatography (g.l.c.): OV 101 at 250° produced one peak.

Nuclear magnetic resonance spectrum (NMR) was as follows: $^1$H (p.p.m. from TMS in CDCl$_3$, integral, number of peaks): 7.30, 10H, s; 4.40, 2H, m; 4.00–3.00, 6H, m; 2.95–2.40, 2H, m; 1.60–0.70, 10H, m.

Mass spectrum (MS), chemical ionisation: m+1, 359.

(iv) and (v)

1-(4-Bromophenyl)-3-methyl-4-n-propyl-2,6-dioxa-7-thiabicyclo[2,2,2]octane (an oil) was prepared from 3-benzyloxymethyl-3-benzylthiomethyl-hexan-2-ol and trimethyl 4-bromo-orthobenzoate using the methodology of stages (iii) and (iv) of example 10.

Nuclear magnetic resonance spectrum (NMR) was as follows: $^1$H (p.p.m. from TMS in CDCl$_3$, integral, number of peaks): 7.40, 4H, s; 4.60–3.90, 3H, m; 3.00, 2H, m; 1.60–0.80, 10H, m.

Mass spectrum (MS), chemical ionisation: m+1, 343, 345

EXAMPLE 15

1-(4-Iodophenyl)-4-n-propyl-2,6-dioxa-7-thiabicyclo[2,2,2]octane (i) n-Butyllithium (16 ml., 1.6M solution in hexane) was added to a stirred solution of 1-(4-bromophenyl)-4-n-propyl-2,6-dioxa-7-thiabicyclo[2,2,2]octane (1.7 g.) in dry diethyl ether (150 ml.) at −70°, under nitrogen. The reaction mixture was allowed to warm up slowly to room temperature and the progress of reaction was monitored by g.l.c. analysis. When all the starting material had disappeared iodine (6.6 g.) in dry diethyl ether (50 ml.) was added and this was followed immediately by the addition of an aqueous solution of sodium thiosulphate (10 g. in 70 ml. water). The mixture was extracted with ethyl acetate. The organic layer was washed with water and dried over anhydrous magnesium sulphate. The solvent was removed in vacuo.

The residue was purified by chromatography on alumina (alumina Woelm TSC) eluting with 1:10 dichloromethane:hexane, saturated with ammonia.

1-(4-Iodophenyl)-4-n-propyl-2,6-dioxa-7-thiabicyclo[2,2,2]octane was obtained as colourless crystals (0.8 g. m.pt. 128-132°).

Nuclear magnetic resonance spectrum (NMR) was as follows: $^1$H (p.p.m. from TMS in CDCl$_3$, integral, number of peaks, $J_{Hz}$): -7.70, 2H, d, 7; 7.40, 2H, d, 7; 4.15, 4H, m; 3.10, 2H, m; 1.30, 4H, m; 0.95, 3H, m.

Mass spectrum (MS), chemical ionisation; m+1 377

EXAMPLE 16

1-(4-Cyanophenyl)-4-cyclohexyl-7-methyl-2,6-dioxa-7-aza-bicyclo[2,2,2]octane (i) Diethyl cyclohexylmalonate (18.7 g.) was added to a stirred suspension of sodium hydride (4.8 g. 50% dispersion in oil) in dry tetrahydrofuran (50 ml) under nitrogen. The mixture was refluxed, with stirring, for one hour. The mixture was cooled and benzyl chloromethyl ether (13.9 g.) in dry tetrahydrafuran (50 ml) was added and the mixture was refluxed, with stirring, for three hours. The mixture was cooled and poured into water. The aqueous mixture was extracted with ether. The ether extracts were washed with water, dried over anhydrous magnesium sulphate and evaporated in vacuo. Diethyl 2-benzyloxymethyl-2-cyclohexyl-malonate (30 g.) was obtained as a brown oil and was used without further purification.

(ii) Diethyl 2-benzyloxymethyl-2-cyclohexyl-malonate (2 g.) was added to a suspension of lithium aluminium hydride (0.63 g.) in dry ether (30 ml), at 0°, under nitrogen. The mixture was stirred at room temperature for twelve hours. Water (5 ml) was added carefully and the mixture was stirred for ten minutes. 10% sulphuric acid solution (10 ml) was added and the mixture was extracted with ether. The ether extracts were washed with water, dried over anhydrous magnesium sulphate and evaporated in vacuo. The residue was purified by chromatography on silica, eluting with 1:1 ether:hexane. 2-Benzyloxymethyl-2-cyclohexyl-propan-1,3-diol was obtained as a colourless oil (1.0 g.).

Gas-liquid chromatography (g.l.c.): OV210 at 230° produced one peak.

Nuclear magnetic resonance spectrum (NMR) was as follows: $^1$H (ppm from TMS in CDCl$_3$, integral, number of peaks, $J_{Hz}$): 7.35, 5H, s; 4.55, 2H, s; 3.75, 4H, d, 6; 3.60, 2H, s; 2.90, 2H, t, 6; 2.00-0.90, 11H, m.

(iii) 2-Benzyloxymethyl-2-cyclohexyl-propan-1,3-diol (5.5 g.) in dry diethyl ether (50 ml.) was added to liquid ammonia (200 ml) at −70°. Sodium (2.5 g.) was added to the stirred solution. Stirring was maintained at −70°, for 1 hour. The mixture was allowed to warm up to 0° and solid ammonium chloride (15 g.) was added cautiously. The ammonia was removed from the reaction mixture under a current of nitrogen. Methanol (25 ml.) was added to the stirred mixture to destroy residual sodium. Dichloromethane (400 ml) was added and the mixture was filtered. The filtrates were evaporated in vacuo. 2-Cyclohexyl-2-hydroxymethyl-propan-1,3-diol was obtained as a colourless solid (3.2 g.).

Nuclear magnetic resonance spectrum (NMR) was as follows: $^1$H (ppm from TMS in CDCl$_3$, integral, number of peaks): 3.80, 6H, s; 3.30, 3H, s; 2.00-0.80. 11H, m.

(iv) A mixture of 2-cyclohexyl-2-hydroxymethylpropane-1,3-diol (3.76 g), ethyl carbonate (2.42 ml) and a solution of potassium hydroxide in ethanol (0.1 ml of a solution of 5 g in 25 ml) were refluxed for 20 minutes. The apparatus was converted to distillation. Ethanol was removed by distillation (78°-80° C. at 760 mmHg). When all the ethanol had been removed the residue was distilled at reduced pressure, 3-cyclohexyl-3-hydroxymethyloxetane distilled as a colourless oil.

Nuclear magnetic resonance spectrum (NMR) was as follows: $^1$H (p.p.m. from TMS in CDCl$_3$, integral, number of peaks, $J_{Hz}$): 4.50, 4H, s; 3.75, 2H, d, 6; 2.6, 1H, t, 6; 2.00-1.00, 11H, m.

Infrared spectrum (IR) liquid film: 3400 (s and br), 1150(s), 970(s),

Mass spectrum (MS), chemical ionisation: m+1 171.

(v) 3-Cyclohexyl-3-hydroxymethyloxetane (7.0 g) was dissolved in dry dichloromethane (20 ml) and added dropwise to a mixture of oxalyl chloride (1.1 eq, 4 ml) in dry dichloromethane (15 ml). At −70° C. a solution of dimethyl sulphoxide (7.15 ml) in dichloromethane (10 ml) was added. After stirring at −70° C. for 30 minutes triethylamine (29 ml) was added over 30 minutes. The reaction mixture was allowed to warm up to room temperature over a period of 3 hours and then quenched in water. Extraction with dichloromethane, followed by washing with dilute hydrochloric acid, saturated sodium bicarbonate solution and brine and drying over magnesium sulphate gave a solution which was evaporated to give 3-cyclohexyl-3-formyloxetane as a colourless oil.

Nuclear magnetic resonance spectrum (NMR) was as follows: $^1$H (p.p.m. from TMS in CDCl$_3$, integral, number of peaks, $J_{Hz}$): 9.80, 1H, s; 4.68, 2H, d, 6; 4.50, 2H, d, 6; 2.05-1.00, 11H, m.

Infrared spectrum (IR) liquid film 1720(s), 980(s).

(vi) 3-Cyclohexyl-3-formyloxetane (1.7 g) was dissolved in methanol (10 ml) at 25° C. In succession, anhydrous sodium acetate (3.3 g), methylamine hydrochloride (3.4 g) and sodium cyanoborohydride (630 mg) were added, followed by a further volume of methanol (30 ml). The mixture was stirred overnight and then basified with sodium hydroxide solution (1M, 22 ml) to pH9. Ether extraction, washing and drying, followed by evaporation gave 3-cyclohexyl-3-methylaminomethyloxetane as a colourless oil.

Nuclear magnetic resonance spectrum (NMR) was as follows: (p.p.m. from TMS in CDCl$_3$, integral, number of peaks, $J_{Hz}$): 4.49, 2H, d, 5; 4.35, 2H, d, 5; 2.75, 2H, s; 2.50, 3H, s; 2.05-1.10, m, (11H).

Infrared spectrum (IR) liquid film 3300(w) and (br), 980(s).

Mass spectrum (MS), chemical ionisation: M+1 184

(vii) 4-Cyanobenzoyl chloride (0.166 g) in dichloromethane (5 ml) was added to a stirred solution of 3-cyclohexyl-3-methylaminomethyl oxetane (0.183 g) and triethylamine (0.42 ml) in dichloromethane (5 ml) at 0° C. After stirring overnight the reaction mixture was poured into saturated sodium bicarbonate solution. Extraction with ether gave crude product which was purified by chromatography on alumina, eluting with dichloromethane:hexane (1:1) saturated with ammonia.

3-[N-(4-Cyanobenzoyl)-N-methylaminomethyl]-3-cyclohexyloxetane was obtained as a colourless oil.

Nuclear magnetic resonance spectrum (NMR) was as follows: (p.p.m. from TMS in CDCl$_3$, integral, number of peaks, J$_{Hz}$): 7.75, 2H, d, 8; 7.50, 2H, d, 8; 4.54, 4H, S; 3.73, 2H, s; 3.09, 3H, s; 2.05–0.95, 11H, m.

Infrared spectrum (IR) liquid film 2220(s) 1640(s) 1070(m) 980(m)

Mass spectrum (MS), chemical ionisation; M+1 313

(viii) Boron trifluoride etherate (37.2 μl) was added to a stirred solution of 3-[N-(4-cyanobenzoyl)-N-methylaminomethyl]-3-cyclohexyloxetane (281 mg) in dichloromethane (3 ml) at −70° C. under nitrogen. After stirring overnight a further portion of boron trifluoride etherate (110 μl) was added. After stirring for a further 24 hours the reaction mixture was poured into dichloromethane (20 ml, saturated with ammonia). Filtration and evaporation of the filtrate gave 1-(4-cyanophenyl)-4-cyclohexyl-7-methyl-2,6-dioxa-7-aza-bicyclo[2,2,2]octane as pale yellow crystals.

Nuclear Magnetic resonance spectrum (NMR) was as follows: (ppm from TMS in CDCl$_3$, integral, number of peaks). 7.60, 4H, s; 3.95, 4H, s; 2.95, 2H, s; 2.04, 3H, s, 1.90–1.00, 11H, m.

Infrared Spectrum (IR) (nujol mull): 2220(s) 1140(m) 1080(s) 1030(m) 990(m)

Mass spectrum (MS), chemical ionisation: M+1 313.
References:
1. V. Gash J. Org. Chem. 1972, 37, 2197
1a. W. E. Conrad, L. A. Levasseur, R. F. Murphy N. L. Hare and H. E. Conrad J. Org. Chem, 1962, 27, 2227
2. S. M. McElvain and J. T. Venerable J. Amer. Chem. Soc. 1950, 72, 1661
3. S. M. McElvain and R. E. Starn J. Amer. Chem. Soc. 1955, 77, 4571
4. Y. Ozoe and M. Eto, Agric. Biol. Chem. 1982, 46, 411
5. J. L. Wood and V. du Vigneaud J. Biol. Chem. 1939, 131, 267
6. I. Vlattas, L. D. Vecchia and J. J. Fitt J. Org. chem. 1973, 38, 3749

Characterising data for various compounds of the invention are set out in the Table below.

| Comp. No. | Y$^1$ | Y | Z | R | R$^1$ | R$^2$ | R$^3$ | mpt | Mass Spectrum Chemical Ionisation (M + 1) | Infrared Spectrum | Synthesis Example |
|---|---|---|---|---|---|---|---|---|---|---|---|
| 1 | O | O | CH$_2$CH$_2$ | Et | H | 4-Clphenyl | H | 78° | 253 | 1130(s),1100(m),1090(m), 1070(m),1020(s). | 1 |
| 2 | O | O | CH$_2$CH$_2$ | n-Pr | H | 4-Clphenyl | H | 94° | 267 | 1130(s),1080(m),1020(s) | 1 |
| 3 | S | O | CH$_2$O | Et | H | 4-Brphenyl | H | solid | 315 317 | 1090(s),1035(m),1022(w) | 2 |
| 4 | S | O | CH$_2$O | n-Pr | H | 4-Brphenyl | H | solid | 329 331 | 1080(s),1040(s),1020(m) | 2 |
| 5 | O | O | CH$_2$CH$_2$O | n-Pr | H | cyclohexyl | H | oil | 255 | 1114(s),1070(s),1040(s) 1010(m) | 3 |
| 6 | O | O | CH$_2$CH$_2$ | t-Bu | H | 4-Clphenyl | H | 155° | 281 | 1130(s),1100(s),1015(s) | 4 |
| 7 | O | O | CHOHCH$_2$ | Et | H | 4-Clphenyl | H | 97° | 269 | 3450(s and br),1130(m), 1100(s),1080(s),1020(m) | 5 |
| 8 | O | O | CHOHCH$_2$ | n-Pr | H | 4-Clphenyl | H | waxy solid | 283 | 3470(s and br),1130(m), 1100(s),1030(s) | 5 |
| 9 | O | O | CHOMeCH$_2$ | n-Pr | H | 4-Clphenyl | H | solid | 297 | | 6 |
| 10 | O | O | CHOAcCH$_2$ | n-Pr | H | 4-Clphenyl | H | waxy solid | 325 | | 7 |
| 11 | O | O | COCH$_2$ | n-Pr | H | 4-Clphenyl | H | 96° | 281 | 1750(s),1130(m),1100(m), 1030(m),1010(m) | 8 |
| 12 | O | O | CH(OSO$_2$Me)CH$_2$ | n-Pr | H | 4-Clphenyl | H | solid | 361 | | 9 |
| 13 | S | O | CH$_2$O | i-Bu | H | 4-Brphenyl | H | 135–138° | 343 345 | | 10 |
| 14 | S | O | CH$_2$O | i-Pr | H | 4-Brphenyl | H | solid | 329 331 | 1080(s),1040(s),1020(s) | 10 |
| 15 | S | O | CH$_2$O | s-Bu | H | 4-Brphenyl | H | solid | 343 345 | 1080(m),1045(s),1020(m) | 10 |
| 16 | S | O | CH$_2$O | s-Bu | H | 4-Clphenyl | H | solid | 299 | 1045(s) | 10 |
| 17 | S | O | CH$_2$O | s-Bu | H | cyclohexyl | H | solid | 271 | 1035(s) | 10 |
| 18 | S | O | CH$_2$O | n-Pr | Me | 4-Brphenyl | H | 120–121° | 343 345 | 1090(s) 1032(s),1020(s) | 10 |
| 19 | S | O | CH$_2$O | n-Pr | Me | cyclohexyl | H | oil | 271 | 1080(m),1060(s),1030(s) | 10 |
| 20 | S | O | CH$_2$O | i-Bu | Me | 4-Brphenyl | H | 101–102° | 357 359 | 1090(s),1050(s),1025(s) | 10 |
| 21 | S | O | CH$_2$O | t-Bu | H | 4-Brphenyl | H | 193–5° | 343 345 | 1095(m),1045(s),1020(s) | 11 |
| 22 | S | O | CH$_2$O | t-Bu | H | 4-Clphenyl | H | 162–4° | 299 | 1100(m),1043(s),1028(s) | 11 |
| 23 | S | O | CH$_2$O | t-Bu | H | cyclohexyl | H | 140–1° | 271 | 1090(m),1040(s),1012(s) | 11 |
| 24 | S | O | CH$_2$O | t-Bu | H | cycloheptyl | H | 142–3° | 285 | 1080(m),1020(m),995(s) | 11 |
| 25 | S | O | CH$_2$S | i-Bu | H | 4-Clphenyl | H | solid | 315 | | 12 |
| 26 | S | O | CH$_2$S | n-Pr | H | 4-Brphenyl | H | solid | 345 347 | | 12 |
| 27 | S | S | CH$_2$S | n-Pr | H | cyclohexyl | H | oil | 289 | | 13 |
| 28 | S | O | CH$_2$O | n-Pr | H | 4-Brphenyl | Me | oil | 343 345 | 1070(s),1010(s) | 14 |
| 29 | S | O | CH$_2$O | n-Bu | H | 4-Brphenyl | H | 110–112° | 343 345 | | 10 |
| 30 | S | O | CH$_2$O | n-Pr | H | 4-Iphenyl | H | 128–132° | 377 | | 15 |
| 31 | O | NMe | CH$_2$O | cyclohex | H | 4-CNphenyl | H | solid | 313 | 2220(s),1140)m),1080(s), 1030(m),990(m) | 16 |

(i) BIOLOGICAL ACTIVITY

A. Lethal Activity Against Houseflies

The activity of compounds of the invention against unanaesthatised female *Musca domestica* (WRL strain), was demonstrated by the topical application to the test insect of a solution of the compound under test in butanone.

The activity of the test compound was also assessed when applied topically in conjunction with the synergist piperonyl butoxide (6 μg PB per insect). Mortality was assessed after 24 and 48 hours.

The following compounds were active at less than 30 μg/fly: 2, 3, 6, 8, 11, 14, 17, 18, 19, 20, 23, 27, 29, 30

The following compounds were active at less than 1 μg/fly: 4, 13, 15, 21, 22, 24, 25, 28

B. Lethal Activity Against *Blattella germanica*

The activity of compounds of the invention against anaesthetised male *Blattella germanica* (WRL strain) was demonstrated by the topical application to the test insect of a solution of the compound under test in butanone.

The activity of the test compound was assessed when applied topically in conjunction with the synergist piperonyl butoxide (10 μg PB per insect). Mortality was assessed after 24 and 48 hours.

The following compounds were active at less than 50 μg/insect: 2, 3, 8, 9, 14, 15, 17, 18, 19, 20, 21, 22, 23

The following compounds were active at less than 5 μg/insect: 4, 13

C. Lethal Activity Against *Sitophilus granarius*

The activity of the compounds of the invention against *S. granarius* adults was demonstrated by addition of the compound in acetone solution to grain, to which the insects were later infested. Mortality was assessed after 6 days.

The following compounds gave activity at less than 200 ppm solution of acetone: 4, 15, 16, 17, 18, 19, 20, 21, 22, 23, 27, 29, 30

The following comnpounds gave activity at less than 50 ppm solution of acetone: 13, 14, 25

D. Lethal Activity Against *Culex quinquefasciatus*

The activity of the compounds of the invention against female Culex adults were demonstrated by direct spraying of 0.5 ml of compound in OPD/Methylene chloride. Mortality was assessed after 24 hours.

The following compounds were active at less than 1.0%: 4, 5, 13, 14, 15, 16, 19, 21, 22, 25, 27, 28, 30

E. Mammalian Toxicity

Compound 4 has an $LD_{50}$ of greater than 200 mg/kg when given orally to mice (Charles River CD1).

The following schemes serve to illustrate the preparation of intermediates used in the preparation compounds of the present invention.

Alk=alkyl, R, $R^1$, $R^2$ etc. are as defined in the specification:

SCHEME 1

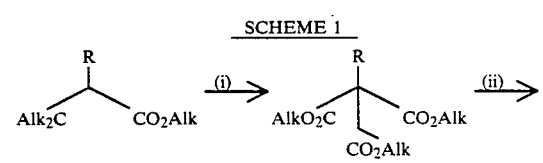

(i) NaH, benzene, BrCH₂CO₂alk
(ii) LiAlH₄, ether

SCHEME 2

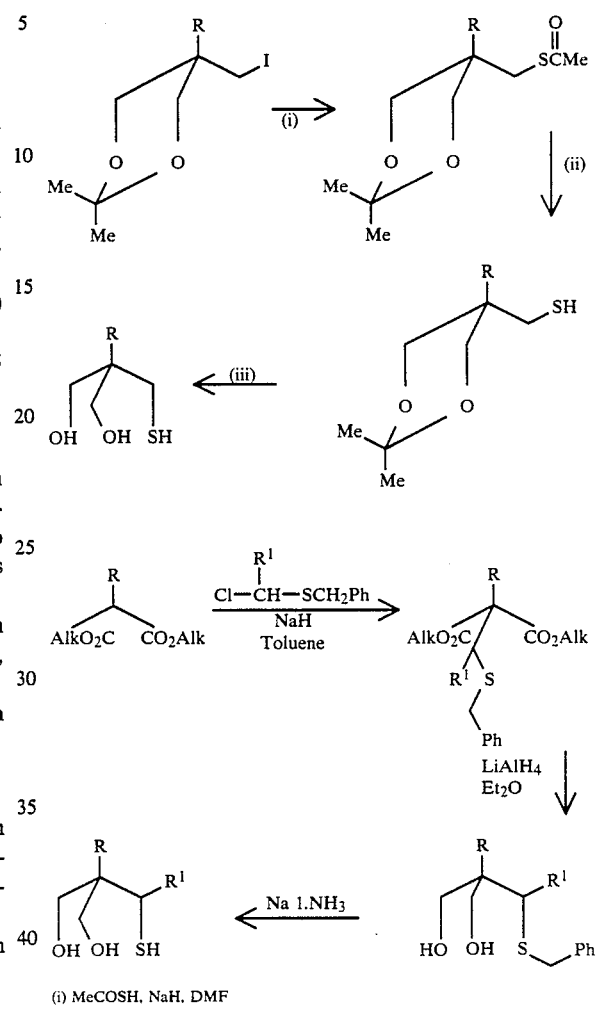

(i) MeCOSH, NaH, DMF
(ii) NaOH, MeOH, H₂O
(iii) Dowex 50 × 8-200, MeOH, H₂O

SCHEME 3

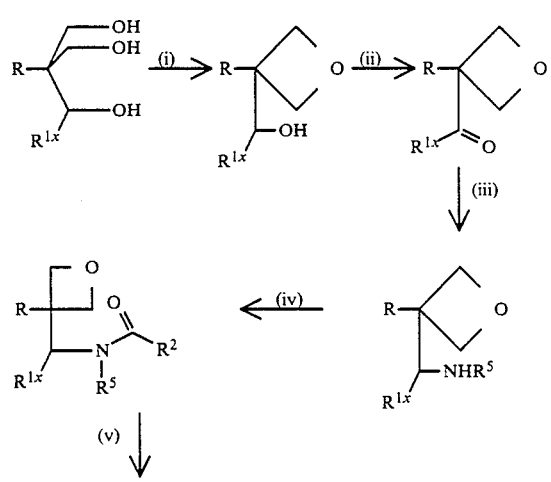

4,985,582
-continued SCHEME 3
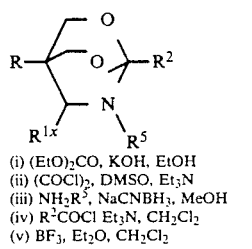
(i) (EtO)$_2$CO, KOH, EtOH
(ii) (COCl)$_2$, DMSO, Et$_3$N
(iii) NH$_2$R$^5$, NaCNBH$_3$, MeOH
(iv) R$^2$COCl Et$_3$N, CH$_2$Cl$_2$
(v) BF$_3$, Et$_2$O, CH$_2$Cl$_2$
-continued SCHEME 5
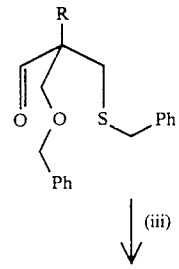
SCHEME 4
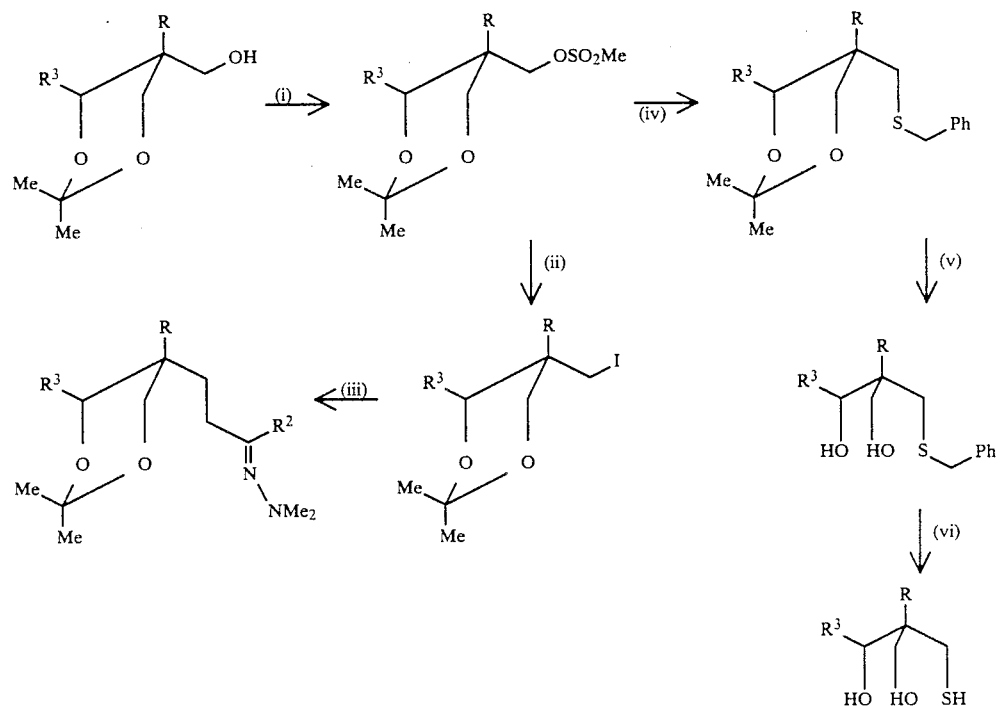
(i) MeSO$_2$Cl, pyridine
(ii) NaI, EtCOMe
(iii) MeCR$^2$, nBu—Li
       ‖
       NNMe$_2$
(iv) NaH, PhCH$_2$SH, DMF
(v) H$^+$ ion exchange resin
(vi) Na, 1NH$_3$
SCHEME 5
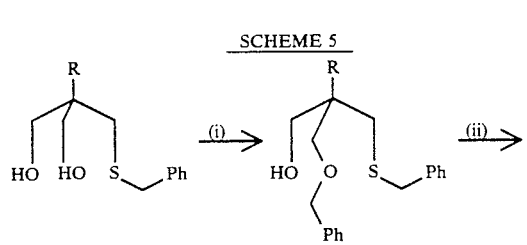
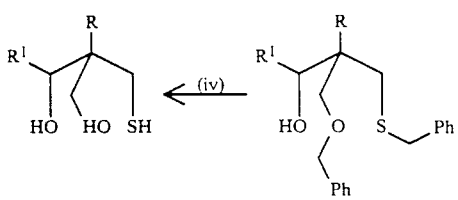
(i) NaH, THF, PhCH$_2$Br
(ii) PCC, CH$_3$CO$_2$Na, CH$_2$Cl$_2$
(iii) R$^1$MgI, Et$_2$O
(iv) Na.1NH$_3$ SCHEME 6
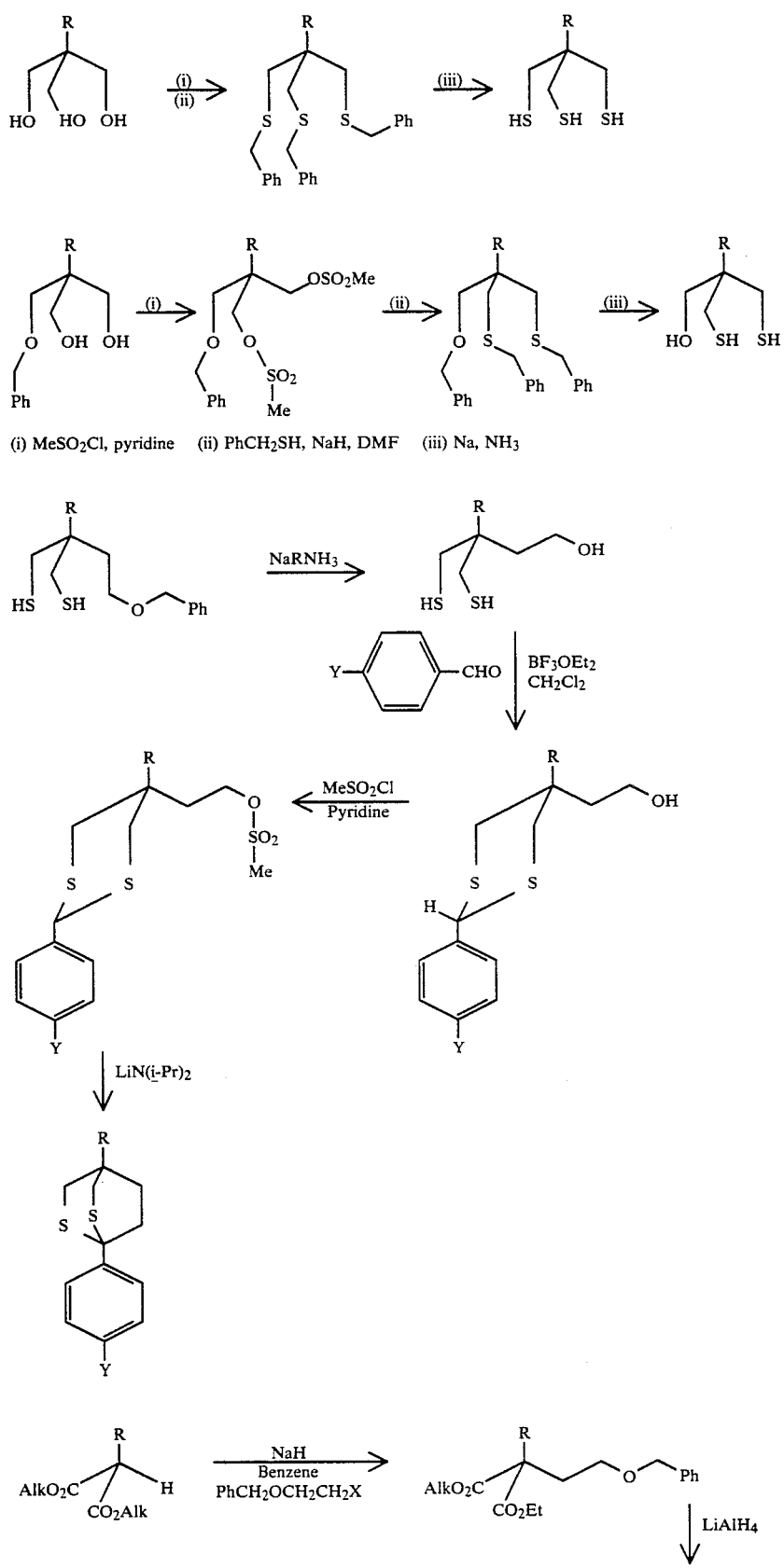
(i) MeSO₂Cl, pyridine   (ii) PhCH₂SH, NaH, DMF   (iii) Na, NH₃

-continued
SCHEME 6

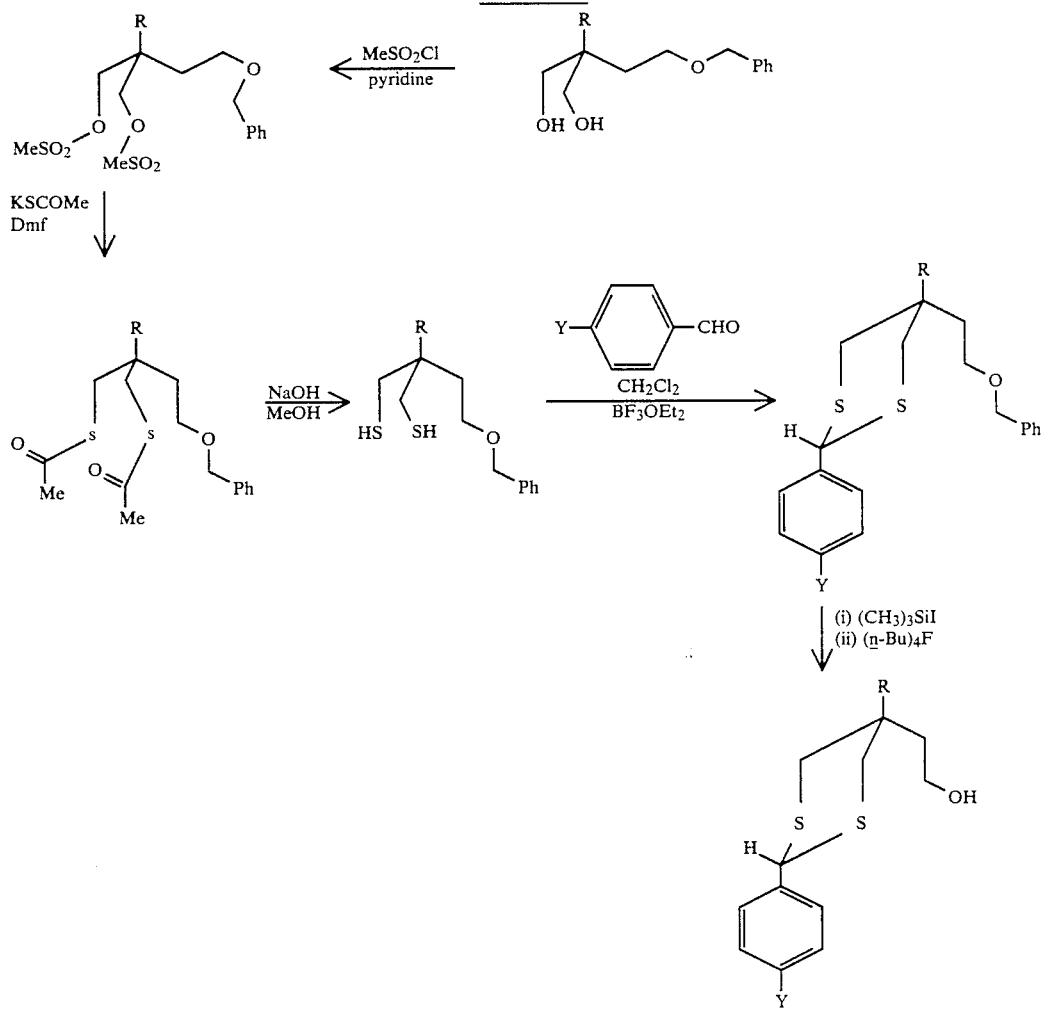

x - leaving group such as halogen

| Formulations | |
|---|---|
| 1. Emulsifiable Concentrate | |
| Compound of formula (I) | 10.00 |
| Ethylan KEO | 20.00 |
| Xylene | 67.50 |
| Butylated Hydroxyanisole | 2.50 |
| | 100.00 |
| 2. Wettable Powder | |
| Compound of formula (I) | 25.0 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
| | 100.00 |
| 3. Dust | |
| Compound of formula (I) | 0.50 |
| Butylated Hydroxyanisole | 0.10 |
| Talc | 99.40 |
| | 100.00 |
| 4. Bait | |
| Compound of formula (I) | 40.25 |
| Icing Sugar | 59.65 |
| Butylated hydroxy toluene | 0.10 |
| | 100.00 |
| 5. Lacquer | |
| Compound of formula (I) | 2.5 |

| -continued | |
|---|---|
| Formulations | |
| Resin | 5.0 |
| Butylated Hydroxy anisole | 0.5 |
| High aromatic white spirit | 92.0 |
| | 100.00 |
| 6. Aerosol | |
| Compound of formula (I) | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |
| 7. Spray | |
| Compound of formula (I) | 0.1 |
| Butylated Hydroxy anisole | 0.1 |
| Xylene | 10.0 |
| Odourless Kerosene | 89.8 |
| | 100.00 |
| 8. Potentiated Spray | |
| Compound of formula (I) | 0.1 |
| Piperonyl Butoxide | 0.5 |
| Butylated Hydroxyanisole | 0.1 |
| Xylene | 10.1 |
| Odourless Kerosene | 89.2 |
| | 100.0 |

We claim:
1. A compound of the formula:
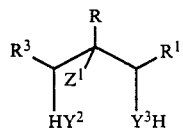
wherein R is propyl, butyl, pentyl, $C_{2-5}$ alkenyl or alkynyl, $C_{3-10}$ cycloalkyl, phenyl or phenyl substituted by halo;
$R^1$ is hydrogen, cyano, $C_{2-3}$ alkynyl, methyl, ethyl, methyl or ethyl substituted by fluoro, cyano, methoxy or methylthio;
$R^3$ is hydrogen;
$Y^2$ and $Y^3$ are each S; and
$Z^1$ is $CH_2SH$.
* * * * *